United States Patent [19]

Rosenbaum et al.

[11] 4,391,603
[45] Jul. 5, 1983

[54] HYDROXYL DERIVATIVES OF BENZALDEHYDE FOR COLORING KERATIN FIBRES IN THE ABSENCE OF OXIDIZING AGENT

[75] Inventors: Georges Rosenbaum, Asnieres; Jean F. Grollier, Paris; Jean Cotteret, Franconville, all of France

[73] Assignee: L'Oreal, Paris, France

[21] Appl. No.: 254,514

[22] Filed: Apr. 15, 1981

[30] Foreign Application Priority Data

Apr. 17, 1980 [FR] France .............................. 80 08645

[51] Int. Cl.³ .............................................. A61K 7/13
[52] U.S. Cl. .......................................... 8/424; 8/405;
8/406
[58] Field of Search .................................... 8/405, 424

[56] References Cited

U.S. PATENT DOCUMENTS

| 2,944,869 | 7/1960 | Kaldpississ et al. | 8/424 |
| 3,893,803 | 7/1975 | Kaiser | 8/424 |
| 3,957,424 | 5/1976 | Zeffren et al. | 8/424 |

FOREIGN PATENT DOCUMENTS 2830497 1/1980 Fed. Rep. of Germany .
2932489 6/1980 Fed. Rep. of Germany .
2057019 3/1981 United Kingdom .

*Primary Examiner*—A. Lionel Clingman
*Attorney, Agent, or Firm*—Cushman, Darby & Cushman

[57] ABSTRACT

The invention discloses the use of hydroxyl derivatives of benzaldehyde for coloring keratin fibres without an oxidizing agent. These derivatives are of the type which correspond to the formula:

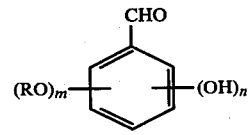

in which R denotes a linear or branched lower alkyl group which is optionally substituted by one or two OH groups, n is equal to 1, 2 or 3, m is equal to 0, 1 or 2 and the sum n+m is equal to 2 or 3.

17 Claims, No Drawings

HYDROXYL DERIVATIVES OF BENZALDEHYDE FOR COLORING KERATIN FIBRES IN THE ABSENCE OF OXIDIZING AGENT

DESCRIPTION

The present invention relates to the use of hydroxyl derivatives of benzaldehyde for colouring keratin fibres, as well as colouring processes and dyeing compositions in which these compounds are used.

Certain benzaldehyde derivatives have already been used in hair dyeing as oxidation dyestuffs, that is to say as compounds which only lead to coloured derivatives on oxidation by means of oxidising reagents, such as hydrogen peroxide or per-salts.

Thus, a dyeing process has been proposed using protocatechuic aldehyde, the shade being developed by means of inorganic oxidising agents chosen from alkali metal or ammonium iodates, periodates and persulphates.

We have now discovered that, surprisingly, a specific class of benzaldehydes makes it possible to colour keratin fibres, and in particular human hair, directly, without using an oxidising agent.

When they are used in this way, these compounds give rise to dyes having a good resistance to light, washing, adverse weather conditions and perspiration.

Some of these compounds are particularly useful for obtaining colorations in yellow shades.

The present invention thus relates to the use of these hydroxyl derivatives of benzaldehyde for colouring keratin fibres and in particular human hair.

The benzaldehyde derivatives used for colouring keratin fibres according to the present invention correspond to the general formula (I):

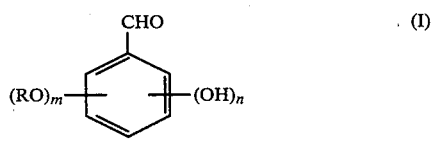

in which R denotes a linear or branched lower alkyl group, preferably having 1 to 4 carbon atoms, which is optionally substituted by one or two hydroxyl groups, n is equal to 1, 2 or 3, m is equal to 0, 1 or 2 such that the sum n+m is equal to 2 or 3, with the proviso that if m is equal to 0 and n is equal to 2 or 3, the OH groups occupy the following positions of the ring:

| 2 | 3 | 4 | 5 | 6 |
|---|---|---|---|---|
|    | OH | OH |    |    |
| OH |    | OH |    |    |
|    | OH |    | OH |    |
| OH | OH | OH |    |    |
| OH | OH |    |    | OH |
| OH | OH |    | OH |    |
| OH |    | OH |    | OH |
|    | OH | OH | OH |    |
| OH |    |    |    | OH | and if m and n both denote 1, the substituents occupy the following positions of the ring:

| 2 | 3 | 4 | 5 | 6 |
|---|---|---|---|---|
| OH |    |    |    | OR |
| OR | OH |    |    |    |
|    | OH |    | OR |    |
| OH |    |    |    | OR |
| OH |    |    |    | OR |
| OH | OCH₂CH₂OH |    |    |    |
| OH |    |    |    | OCH₂CHCH₂<br>   \|   \|<br>   OH OH |
| OH | OC₂H₅ |    |    |    | or their bisulphite adducts.

The alkyl groups which are more particularly preferred are methyl or ethyl. The expression "bi-sulphite adduct" is to be understood as meaning the adduct resulting from the addition of one equivalent of an alkali metal bisulphite, such as sodium bisulphite or potassium bisulphite, to one equivalent of the hydroxyl derivative of benzaldehyde.

The compounds which are more particularly preferred according to the invention are those corresponding to the formula (I) in which the substituents having the meanings indicated in Table I occupy the positions also shown in Table I.

TABLE I

| Compound No. | 2 | 3 | 4 | 5 | 6 |
|---|---|---|---|---|---|
| 1 |    | OH | OH |    |    |
| 2 | OH |    | OH |    |    |
| 3 | OH |    |    |    | OH |
| 4 |    | OH |    | OH |    |
| 5 | OH | OH | OH |    |    |
| 6 | OH | OH |    |    | OH |
| 7 | OH | OH |    | OH |    |
| 8 | OH |    | OH |    | OH |
| 9 |    | OH | OH | OH |    |
| 10 | OH |    |    |    | OCH₃ |
| 11 | OCH₃ | OH |    |    |    |
| 12 |    | OH | OCH₃ |    |    |
| 13 |    | OH |    | OCH₃ |    |
| 14 | OH |    |    | OC₂H₅ |    |
| 15 | OH | OC₂H₅ |    |    |    |
| 16 | OH | OH | OCH₃ |    |    |
| 17 | OH | OH |    | OCH₃ |    |
| 18 | OH | OH |    |    | OCH₃ |
| 19 | OH | OCH₃ | OH |    |    |
| 20 | OH |    | OH | OCH₃ |    |
| 21 | OH | OCH₃ |    | OH |    |
| 22 | OH |    | OCH₃ | OH |    |
| 23 | OH |    |    | OH | OCH₃ |
| 24 | OH | OCH₃ |    |    | OH |
| 25 |    | OH | OH | OCH₃ |    |
| 26 | OH |    |    | OH | OCH₃ |
| 27 | OH |    | OCH₃ |    | OH |
| 28 | OCH₃ | OH | OH |    |    |
| 29 |    | OH | OH |    | OCH₃ |
| 30 | OCH₃ | OH |    | OH |    |
| 31 |    | OH | OCH₃ | OH |    |
| 32 | OH | OC₂H₅ |    | OH |    |
| 33 |    | OH | OH | OC₂H₅ |    |
| 34 | OH | OCH₃ |    | OCH₃ |    |
| 35 | OCH₃ | OH | OCH₃ |    |    |
| 36 |    | OH | OCH₃ | OCH₃ |    |
| 37 |    | OCH₃ | OH | OCH₃ |    |
| 38 | OH | OCH₃ | OCH₃ |    |    |
| 39 | OH | OCH₃ |    |    | OCH₃ |
| 40 | OH |    | OCH₃ |    | OCH₃ |
| 41 | OH |    |    | OCH₃ | OCH₃ |
| 42 | OCH₃ | OH |    | OCH₃ |    |
| 43 | OCH₃ | OH |    |    | OCH₃ |
| 44 |    | OH | OCH₃ |    | OCH₃ |
| 45 |    | OH |    | OCH₃ | OCH₃ |
| 46 | OCH₃ | OCH₃ | OH |    |    |
| 47 | OCH₃ |    | OH | OCH₃ |    |
| 48 | OCH₃ |    | OH |    | OCH₃ |

TABLE I-continued

| Compound No. | 2 | 3 | 4 | 5 | 6 |
|---|---|---|---|---|---|
| 49 | OH | | OCH$_2$CH$_2$OH | | |
| 50 | OH | | —OCH$_2$CH(OH)—CH$_2$(OH) | | |

The process for colouring keratin fibres, and in particular human hair, according to the invention is characterised in that at least one composition containing, in a cosmetically acceptable medium, a dyestuff corresponding to the formula (I) above is applied to the said fibres, without an oxidising agent.

Although the process can be carried out at pH values of, say, 2 to 11, which are normally used in cosmetics, a preferred embodiment of the invention consists in carrying out the coloration in an acid medium.

Amongst the preferred dyestuffs used in this embodiment of the invention, there may be mentioned the dyestuffs of the formula (I) in which the substituents have the meanings indicated in Table II and occupy the positions of the benzene ring which are also shown in this table.

TABLE II

| 2 | 3 | 4 | 5 | 6 |
|---|---|---|---|---|
|   | OH | OH |   |   |
| OH |   | OH |   |   |
| OH |   |   |   | OH |
| OH | OH | OH |   |   |
| OH | OH |   | OH |   |
| OH | OH |   |   | OH |
| OH |   | OH |   | OH |
|   | OH | OH | OH |   |
| OH | OH | OCH$_3$ |   |   |
| OH | OH |   | OCH$_3$ |   |
| OH | OH |   |   | OCH$_3$ |
| OH | OCH$_3$ | OH |   |   |
| OH |   | OH | OCH$_3$ |   |
| OH | OCH$_3$ |   | OH |   |
| OH |   | OCH$_3$ | OH |   |
| OH |   |   | OH | OCH$_3$ |
| OH | OCH$_3$ |   |   | OH |
|   | OH | OH | OCH$_3$ |   |

It is also possible to carry out the process in an alkaline medium, and the most remarkable results can be obtained with the dyestuffs corresponding to the formula (I) in which the substituents have the meanings indicated in Table III and occupy the positions of the benzene ring which are indicated in this table.

TABLE III

| 2 | 3 | 4 | 5 | 6 |
|---|---|---|---|---|
|   | OH | OH |   |   |
| OH | OH | OH |   |   |
| OH | OH |   | OH |   |
| OH | OH |   |   | OH |
| OH |   | OH |   | OH |
|   | OH | OH | OH |   |
| OH | OCH$_3$ |   | OCH$_3$ |   |
| OCH$_3$ | OH | OCH$_3$ |   |   |
|   | OH | OCH$_3$ | OCH$_3$ |   |
|   | OCH$_3$ | OH | OCH$_3$ |   |

A dyeing process giving particularly valuable results consists in using the benzaldehyde derivatives corresponding to the general formula (I) indicated above, in powder form, mixing them with other solids, such as clay, talc or plant-based fillers, the whole being mixed with a liquid just before application to the hair. According to this embodiment of the invention, a poultice based on the benzaldehyde derivatives is applied to the keratin fibres and in particular human hair, it is left on the hair for, say, 5 to 60 minutes, and the hair is rinsed and dried.

The hair can also be coloured in accordance with processes comprising several steps, at least one of which consists in applying a dyestuff of the formula (I).

The dyeing compositions according to the invention are essentially characterised in that they contain, in a cosmetically acceptable medium, at least one of the derivatives corresponding to the formula (I) indicated above, as a dyestuff.

The compositions which are more particularly preferred according to the invention are those containing a benzaldehyde derivative corresponding to the formula (II)

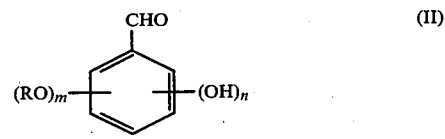

in which R, n and m have the meanings indicated above, n+m being equal to 3, or the compounds of the formula (III)

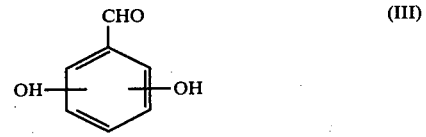

in which the OH groups occupy the 2,6- or 3,5-positions.

The compositions according to the invention generally contain the compounds corresponding to the abovementioned formulae in an amount from 0.05 to 10% by weight and in particular from 0.1 to 5% by weight.

The cosmetically acceptable medium is typically aqueous and its pH is generally 2 to 11, it can be adjusted to the desired value by means of alkalising agents, such as ammonia, alkali metal carbonates, alkanolamines, such as mono-, di- or tri-ethanolamine, or alkylamines, or with acidifying agents, such as hydrochloric acid, sulphuric acid and citric acid.

The dyeing compositions according to the invention can also contain anionic, cationic, non-ionic and/or amphoteric surface-active agents or mixtures thereof. Amongst the surface-active agents which are more particularly preferred, there may be mentioned soaps, alkylbenzenesulphonates, alkylnaphthalenesulphonates, sulphates, ether-sulphates and sulphonates of fatty alcohols, quaternary ammonium salts, such as trimethylcetylammonium bromide and cetylpyridinium bromide, fatty acid diethanolamides, polyoxyethyleneated or polyglycerolated acids, alcohols and amides and polyoxyethyleneated or polyglycerolated alkylphenols. The surface-active agents are typically present in the compositions according to the invention in proportions of 0.1 to 55% by weight and preferably 1 to 40% by weight, relative to the total weight of the composition.

These compositions can also contain organic solvents for solubilising compounds which would not otherwise be sufficiently soluble in water. Amongst these solvents, examples which may be mentioned are lower alkanols, such as ethanol and isopropanol, glycerol, glycols or glycol ethers, such as ethylene glycol monobutyl ether, ethylene glycol, propylene glycol, and diethylene glycol monoethyl ether and monomethyl ether, and also analogous products or mixtures thereof. These solvents are preferably present in proportions from 1 to 50% by weight and more particularly from 3 to 30% by weight, relative to the total weight of the composition. The compositions can also contain anionic, non-ionic, cationic or amphoteric polymers, suitably in proportions from 0.1 to 5% by weight.

The compositions according to the invention can be thickened, preferably with sodium alginate, gum arabic or cellulose derivatives, such as methylcellulose, hydroxyethylcellulose, hydroxypropylmethylcellulose and carboxymethylcellulose, or various polymers serving this purpose, in particular acrylic acid derivatives. It is also possible to use inorganic thickeners, such as bentonite. These thickeners are preferably present in proportions of 0.5 to 5% by weight and in particular 0.5 to 3% by weight, relative to the total weight of the composition.

Antioxidants, such as sodium sulphite, thioglycolic acid, sodium bisulphite, ascorbic acid and hydroquinone, can also be included in the compositions according to the invention. These antioxidants are advantageously present in the composition in proportions of 0.05 to 1.5% by weight, relative to the total weight of the composition. It is of course possible to add to the compositions according to the invention any other adjuvants normally used in hair-dyeing compositions, and in particular penetrating agents, sequestering agents, buffers and perfumes.

It is self-evident that the compositions according to the invention can contain other direct dyestuffs, more particularly anthraquinone dyestuffs, azo dyestuffs, nitro benzene derivatives, indophenols, indamines and indoanilines.

The dyeing compositions according to the invention can be presented in various forms, such as liquids, creams, gels or any other form suitable for dyeing the hair. In particular, they can be packaged in aerosol flasks in the presence of a propellant.

Presentation in the form of a poultice constitutes a particularly preferred embodiment of the invention. In this case, the benzaldehyde derivatives used according to the invention are prepared in the form of a powder which is stable on storage and are incorporated into a solid medium. The term "poultice" is to be understood as meaning a product composed of powders, flours or starchy or mucilaginous substances, mixed with a liquid. The powders can consist of, for example, insoluble substances, such as silicas, powdered plants, clays, and plants powdered after solvent extraction of their active principles. The liquid can be water and/or solvents, such as alcohols, glycols and oils. The viscosity which is generally obtained after mixing is suitably from 100 to 9,000 cps. A particularly preferred embodiment of the invention consists in using the benzaldehyde derivatives of the formula (I), and more particularly: 2,4-dihydroxybenzaldehyde, 3,4-dihydroxybenzaldehyde, 3-hydroxy-4-methoxybenzaldehyde and 4-hydroxy-3,5-dimethoxybenzaldehyde, at the same time as other natural dyestuffs, so as to prepare a dyeing composition for keratin fibres, and preferably for human hair, which is based on natural substances. Natural dyestuffs which may be mentioned more particularly for this purpose are: lawsone, juglone, indigo and the plants or extracts in which these dyestuffs are present.

These compositions can be used as indicated above in hair-dyeing processes carried out in several stages, one step of the process consisting in applying at least one composition of the present invention.

The following Examples further illustrate the present invention.

EXAMPLE 1

The following composition is prepared:

| | |
|---|---|
| 2,3,4-trihydroxybenzaldehyde | 1 g |
| ethylglycol | 10 g |
| water q.s.p. | 100 g |

Hair swatches containing 90% of white hair are dyed with an application time of 30 minutes.

The swatches are rinsed and dried. A very intense yellow-green coloration is obtained.

EXAMPLES 2 TO 10

On replacing the 2,3,4-trihydroxybenzaldehyde by the hydroxyl derivatives of benzaldehyde which are indicated in the following Table IV, the composition containing the amount of ethylglycol also recorded in this table, the colorations shown in the last column of Table IV are obtained.

TABLE IV

| Example | Ethylglycol (g) | Dyestuff | Coloration obtained on 90% white hair |
|---|---|---|---|
| 2 | 10 | 2,4-dihydroxybenzaldehyde | moderately intense yellow-green |
| 3 | 10 | 3,4-dihydroxybenzaldehyde | fairly intense yellow-green |
| 4 | 20 | 2,4,6-trihydroxybenzaldehyde | intense yellow-orange |
| 5 | 10 | 3,4,5-trihydroxybenzaldehyde | intense yellow-green |
| 6 | 10 | 3-hydroxy-4-methoxybenzaldehyde | light yellow-green |
| 7 | 40 | 2-hydroxy-4,6-dimethoxybenzaldehyde | very light yellow-green |
| 8 | 10 | 4-hydroxy-3,5-dimethoxybenzaldehyde | fairly intense yellow-green |
| 9 | 10 | 2,5-dihydroxy-3-methoxybenzaldehyde | intense yellow-orange |
| 10 | 10 | 3,4-dihydroxy-5-methoxybenzaldehyde | fairly intense yellow-green |

EXAMPLE 11

The following dyeing composition is prepared:

| | |
|---|---|
| 3,4-dihydroxybenzaldehyde | 2 g |
| vinylpyrrolidone/crotonic acid (90/10) copolymer | 1.8 g |
| vinylpyrrolidone/vinyl acetate (60/40) copolymer | 0.4 g |
| 96° strength ethyl alcohol q.s.p. | 50° alcoholic strength |
| triethanolamine q.s.p. | pH 6 |
| water q.s.p. | 100 g |

When applied to light blond hair, this wavesetting lotion imparts a slight golden sheen to the hair after drying.

EXAMPLE 12

On adding 0.03 g of 1-N-(δ-aminopropyl)-aminoanthraquinone hydrochloride to the composition of Example 11, it imparts a light coppery blond shade to light blond hair.

EXAMPLE 13

The following composition is prepared:

| | |
|---|---|
| 2-hydroxy-5-methoxybenzaldehyde | 0.3 g |
| 3,4-dihydroxy-5-methoxybenzaldehyde | 0.3 g |
| 1-(4'-nitrophenylazo)-2-methyl-4-(di-β-hydroxyethylamino)-benzene (Disperse Red 17) | 0.4 g |
| N—(2',6'-dimethyl-4'-amino-5'-methoxyphenyl)-2,6-dimethyl-1,4-benzoquinone-imine | 0.05 g |
| vinylpyrrolidone/vinyl acetate (60/40) copolymer | 0.5 g |
| quaternised polyvinylpyrrolidone sold under the name Gafquat 734 by Gaf | 0.4 g |
| tetradecyltrimethylammonium bromide | 0.2 g |
| 96° strength ethyl alcohol q.s.p. | 50° alcoholic strength |
| citric acid q.s.p. | pH 6 |
| water q.s.p. | 100 g |

This composition constitutes a wavesetting lotion, which is applied to natural or coloured, chestnut hair. The hair possesses a mahogany sheen after drying.

EXAMPLE 14

The following composition is prepared:

| | |
|---|---|
| 2,4-dihydroxybenzaldehyde | 1.5 g |
| cetyl alcohol | 17 g |
| cetyl/stearyl alcohol containing 15 mols of ethylene oxide, sold under the name Mergital CS 15/E by Henkel | 6 g |
| Oleyl alcohol sold under the name Océnol HD 80/85 by Henkel | 3 g |
| citric acid q.s.p. | pH 3 |
| water q.s.p. | 100 g |

This cream is applied to natural or coloured, chestnut hair for 20 minutes.
After rinsing, the hair is shampooed and dried.
The hair then possesses a golden sheen.

EXAMPLE 15

The following dyeing composition is prepared:

| | |
|---|---|
| 3,5-dimethoxy-4-hydroxybenzaldehyde | 0.9 g |
| 4-methoxy-3-hydroxybenzaldehyde | 0.5 g |
| 4-N—methylamino-1-N—(γ-aminopropyl)-aminoanthraquinone hydrochloride | 0.025 g |
| synthetic linear $C_{13}$–$C_{15}$ fatty alcohol containing 2.8 mols of ethylene oxide, sold under the name Ukanil 25 by PCUK | 3 g |
| synthetic linear $C_9$–$C_{11}$ fatty alcohol containing 6 mols of ethylene oxide, sold under the name Ukanil 43 by PCUK | 2 g |
| tetradecyltrimethylammonium bromide | 1.5 g |
| ethylglycol | 10 g |
| triethanolamine q.s.p. | pH 5 |
| water q.s.p. | 100 g |

This foaming lotion is applied for fifteen minutes to hair having an unattractive red sheen.
After rinsing and drying, this red sheen has disappeared or has been greatly toned down.

EXAMPLE 16

The following dyeing composition is prepared:

| | |
|---|---|
| 3,4-dihydroxy-5-methoxybenzaldehyde | 0.35 g |
| $N_1$—methyl-$N_4$—methyl-$N_4$—β-hydroxyethyl-2-nitro-para-phenylenediamine | 0.45 g |
| 50/50 mixture of cetyl alcohol and stearyl alcohol, sold under the name lanette wax O by Henkel | 20 g |
| copra monoethanolamide | 5 g |
| 20% pure ammonium lauryl-sulphate sold under the name Sipon LA 30 by Henkel | 10 g |
| 2-amino-2-methylpropanol q.s.p. | pH 8.5 |
| water q.s.p. | 100 g |

This composition, which is in the form of a cream, is applied for 30 minutes to a natural deep blond head of hair which is unsensitised and possesses a significant percentage of white hair.
The colour of the hair after shampooing and drying is revived to its natural shade and the white hair is covered in the same tint.

EXAMPLE 17

The following dyeing composition is prepared:

| | |
|---|---|
| 3,4,5-trihydroxybenzaldehyde | 0.8 g |
| standard methylene green BZ, Fluka (CI Basic Green 5) | 0.011 g |
| 1-amino-4-N—methylamino-2-nitrobenzene | 0.44 g |
| sodium salt of sulphated oxyethyleneated alkanol - 0.6 to 0.65 meq (g) - sold under the name Sadipan 8533 by Lever | 25 g |
| diethanolamide of coconut fatty acid | 5 g |
| butylglycol | 1 g |
| citric acid q.s.p. | pH 6 |
| water q.s.p. | 100 g |

This colouring shampoo can be applied to deep blond or light chestnut hair.
After an application time of 15 minutes and after rinsing and drying, it imparts an attractive mahogany-brown shade to the hair.

EXAMPLE 18

The following dyeing composition is prepared:

| | |
|---|---|
| 2,5-dihydroxy-3-methoxybenzaldehyde | 1.2 g |
| 2-N—β-hydroxyethylamino-5-hydroxynitrobenzene | 0.2 g |
| synthetic linear $C_{13}$–$C_{15}$ fatty alcohol containing 2.8 mols of ethylene oxide, sold under the name Ukanil 25 by PCUK | 3 g |
| synthetic linear $C_9$–$C_{11}$ fatty alcohol containing 6 mols of ethylene oxide, sold under the name Ukanil 43 by PCUK | 2 g |
| tetradecyltrimethylammonium bromide | 1.5 g |
| ethylglycol | 10 g |
| triethanolamine q.s.p. | pH 5 |
| water q.s.p. | 100 g |

This slightly foaming lotion is applied to hair which is chestnut to light chestnut.
After an application time of 15 minutes and after rinsing and drying, a head of hair possessing a coppery sheen is obtained.

EXAMPLE 19

The following dyeing composition is prepared:

| | |
|---|---|
| 2,3,4-trihydroxybenzaldehyde | 0.2 g |
| 1-amino-4-N—methylamino-2-nitrobenzene | 0.2 g |
| 2-amino-5-hydroxynitrobenzene | 0.1 g |
| 2-N—β-hydroxyethylamino-5-methoxynitrobenzene | 0.1 g |
| CI Basic Blue 99 | 0.05 g |
| oxyethyleneated nonylphenol containing 4 mols of ethylene oxide, sold under the name Sinnopal NP 4 by Henkel | 11 g |
| oxyethyleneated nonylphenol containing 9 mols of ethylene oxide, sold under the name Sinnopal NP 9 by Henkel | 11 g |
| propylene glycol | 5.5 g |
| absolute ethyl alcohol | 4 g |
| ammonia q.s.p. | pH 7.5 |
| water q.s.p. | 100 g |

This gel is applied to blond hair for 30 minutes.

After shampooing and drying, a particularly attractive yellow-brown sheen is obtained if the hair has been slightly sensitised beforehand by perming.

EXAMPLE 20

The following composition is prepared:

| | |
|---|---|
| 3,4-dihydroxybenzaldehyde | 1.5 g |
| lawsone | 0.1 g |
| powdered chestnut leaves q.s.p. | 100 g |

This powder is mixed with four times its weight of warm water at the time of use.

The poultice obtained is then applied to a light blond head of hair for 20 minutes and then carefully removed. After shampooing and drying, the hair is embellished with a delicate golden sheen.

EXAMPLE 21

The following composition is prepared:

| | |
|---|---|
| 4-hydroxy-3,5-dimethoxybenzaldehyde | 2 g |
| 2,3-dihydroxybenzaldehyde | 3 g |
| 2-N—β-hydroxyethylamino-5-hydroxynitrobenzene | 0.8 g |
| wheat flour | 10 g |
| rye flour | 10 g |
| feedstuff-quality maize cobs q.s.p. | 100 g |

Five times the weight of warm water is added to this powder at the time of use and the whole is mixed.

The poultice obtained is applied to a light chestnut head of hair. The sheen obtained after shampooing and drying is a coppery sheen.

We claim:

1. Process for colouring keratin fibres in the absence of an oxidising agent, which comprises applying thereto at least one composition containing a cosmetically acceptable medium and a dyestuff corresponding to the formula:

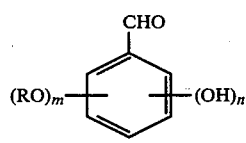

(I)

in which R denotes a linear or branched lower alkyl group which is optionally substituted by one or two hydroxyl groups, n is equal to 1, 2 or 3, m is equal to 0, 1 or 2 such that n+m is equal to 2 or 3, with the proviso that (i) if m is equal to 0 (and n is equal to 2 or 3), the OH groups occupy the following positions of the ring:

| 2 | 3 | 4 | 5 | 6 |
|---|---|---|---|---|
|  | OH | OH |  |  |
| OH |  | OH |  |  |
|  |  | OH | OH |  |
| OH | OH | OH |  |  |
| OH | OH |  |  | OH |
| OH | OH |  | OH |  |
| OH |  | OH |  | OH |
|  | OH | OH | OH |  |
| OH |  |  |  | OH | and (ii) if m and n both denote 1, the substituents occupy the following positions of the rings:

| 2 | 3 | 4 | 5 | 6 |
|---|---|---|---|---|
| OH |  |  |  | OR |
| OR | OH |  |  |  |
|  | OH |  | OR |  |
|  | OH |  |  | OR |
| OH |  |  | OR |  |
| OH | OCH₂CH₂OH (3) |  |  |  |
| OH |  |  | OCH₂CHCH₂ \| \| OH OH (5) |  |
| OH | OC₂H₅ |  |  |  | or a bisulphite adduct thereof.

2. Process according to claim 1 in which the dyestuff corresponds to formula (I) as defined in claim 1 in which the substituents and the position thereof are as specified in the following table:

| Compound No. | 2 | 3 | 4 | 5 | 6 |
|---|---|---|---|---|---|
| 1 |  | OH | OH |  |  |
| 2 | OH |  | OH |  |  |
| 3 | OH |  |  |  | OH |
| 4 |  | OH |  | OH |  |
| 5 | OH | OH | OH |  |  |
| 6 | OH | OH |  |  | OH |
| 7 | OH | OH |  | OH |  |
| 8 | OH |  | OH |  | OH |
| 9 |  | OH | OH | OH |  |
| 10 | OH |  |  |  | OCH₃ |
| 11 | OCH₃ | OH |  |  |  |
| 12 |  | OH | OCH₃ |  |  |
| 13 |  | OH |  | OCH₃ |  |
| 14 | OH |  |  | OC₂H₅ |  |
| 15 | OH | OC₂H₅ |  |  |  |
| 16 | OH | OH |  | OCH₃ |  |
| 17 | OH | OH |  | OCH₃ |  |
| 18 | OH | OH |  |  | OCH₃ |
| 19 | OH | OCH₃ | OH |  |  |
| 20 | OH |  |  | OH | OCH₃ |
| 21 | OH | OCH₃ |  | OH |  |
| 22 | OH |  |  | OCH₃ | OH |
| 23 | OH |  |  | OH | OCH₃ |
| 24 | OH | OCH₃ |  |  | OH |
| 25 |  | OH | OH | OCH₃ |  |
| 26 | OH |  | OH |  | OCH₃ |
| 27 | OH |  | OCH₃ |  | OH |
| 28 | OCH₃ | OH | OH |  |  |
| 29 |  | OH | OH |  | OCH₃ |
| 30 | OCH₃ | OH |  | OH |  |
| 31 |  | OH | OCH₃ | OH |  |
| 32 | OH | OC₂H₅ |  | OH |  |
| 33 |  | OH |  | OH | OC₂H₅ |
| 34 | OH | OCH₃ |  |  | OCH₃ |

-continued

| Compound No. | 2 | 3 | 4 | 5 | 6 |
|---|---|---|---|---|---|
| 35 | OCH$_3$ | OH | | OCH$_3$ | |
| 36 | | OH | | OCH$_3$ | OCH$_3$ |
| 37 | | OCH$_3$ | | OH | OCH$_3$ |
| 38 | OH | OCH$_3$ | OCH$_3$ | | |
| 39 | OH | OCH$_3$ | | | OCH$_3$ |
| 40 | OH | | OCH$_3$ | | OCH$_3$ |
| 41 | OH | | | OCH$_3$ | OCH$_3$ |
| 42 | OCH$_3$ | OH | | OCH$_3$ | |
| 43 | OCH$_3$ | OH | | | OCH$_3$ |
| 44 | | OH | | OCH$_3$ | OCH$_3$ |
| 45 | | OH | | OCH$_3$ | OCH$_3$ |
| 46 | OCH$_3$ | OCH$_3$ | OH | | |
| 47 | OCH$_3$ | | | OH | OCH$_3$ |
| 48 | OCH$_3$ | | | OH | OCH$_3$ |
| 49 | OH | OCH$_2$CH$_2$OH | | | |
| 50 | OH | | | —OCH$_2$CH(OH)—CH$_2$OH | |

3. Process according to claim 1 in which n+m is equal to 3.

4. Process according to claim 1 in which m is 0 and n is 2, the two OH groups being in the 2,6- or 3,5-positions.

5. Process according to claim 1 in which the dyestuff is applied in an acid medium.

6. Process according to claim 5, in which the dyestuff of formula (I) is one in which the substituents and the position thereof are as specified in the following table:

| 2 | 3 | 4 | 5 | 6 |
|---|---|---|---|---|
| | OH | OH | | |
| OH | | OH | | |
| OH | | | | OH |
| OH | OH | OH | | |
| OH | OH | | OH | |
| OH | OH | | | OH |
| OH | | OH | | OH |
| | OH | OH | OH | |
| OH | OH | OCH$_3$ | | |
| OH | OH | | OCH$_3$ | |
| OH | OH | | | OCH$_3$ |
| OH | OCH$_3$ | OH | | |
| OH | | OH | OCH$_3$ | |
| OH | OCH$_3$ | | OH | |
| OH | | OCH$_3$ | OH | |
| OH | | | OH | OCH$_3$ |
| OH | OCH$_3$ | | | OH |
| | OH | OH | OCH$_3$ | |

7. Process according to claim 1, in which the dyestuff is applied in an alkaline medium.

8. Process according to claim 7, in which the dyestuff of formula (I) is one in which the substituents and the position thereof are as specified in the following table:

| 2 | 3 | 4 | 5 | 6 |
|---|---|---|---|---|
| | OH | OH | | |
| OH | OH | OH | | |
| OH | OH | | OH | |
| OH | OH | | | OH |
| OH | | | | OH |
| | OH | OH | OH | |
| OH | OCH$_3$ | | OCH$_3$ | |
| OCH$_3$ | OH | OCH$_3$ | | |
| | OH | OCH$_3$ | OCH$_3$ | |
| | OCH$_3$ | OH | OCH$_3$ | |

9. Process according to claim 1, in which the dyestuff is applied in the form of a poultice with one or more powdered solids, and after the fibres have been impregnated, they are rinsed and dried.

10. A composition suitable for dyeing keratin fibres, which contains, in a diluent or carrier, at least one dyestuff corresponding to the formula defined in claims 1 or 2.

11. A composition according to claim 10, in which the dyestuff is one in which n+m is equal to 3.

12. A composition according to claim 11, in which the dyestuff is one in which m is 0 and n is 2, the two OH groups being in the 2,6- or 3,5-positions.

13. A composition according to claim 10, in which the dyestuff is 2,4-dihydroxybenzaldehyde, 3,4-dihydroxybenzaldehyde, 3-hydroxy-4-methoxybenzaldehyde or 4-hydroxy-3,5-dimethoxybenzaldehyde.

14. A composition according to claim 10 which is in the form of a poultice powder comprising a clay, silica, flour, starchy or mucilaginous substance and a powdered plant.

15. A composition according to claim 10 which contains one or more direct dyestuffs and/or other natural dyestuffs.

16. A composition according to claim 10 in which the diluent is aqueous and contains one or more surface-active agents, organic solvents, thickeners, antioxidants, penetrating agents, sequestering agents, film-forming polymers, buffers, alkalising or acidifying agents or perfumes.

17. A composition according to claim 10 in which the dyestuff of formula I is present in an amount from 0.05 to 10% by weight.

* * * * *